US010076349B2

(12) United States Patent
Voic

(10) Patent No.: US 10,076,349 B2
(45) Date of Patent: Sep. 18, 2018

(54) ULTRASONIC SURGICAL DRILL AND ASSOCIATED SURGICAL METHOD

(71) Applicant: Misonix Incorporated, Farmingdale, NY (US)

(72) Inventor: Dan Voic, Cedar Grove, NJ (US)

(73) Assignee: MISONIX, INC., Farmingdale, NY (US)

( * ) Notice: Subject to any disclaimer, the term of this patent is extended or adjusted under 35 U.S.C. 154(b) by 724 days.

(21) Appl. No.: 13/833,385

(22) Filed: Mar. 15, 2013

(65) Prior Publication Data

US 2014/0277028 A1     Sep. 18, 2014

(51) Int. Cl.
A61B 17/16      (2006.01)
A61B 17/32      (2006.01)

(52) U.S. Cl.
CPC .. *A61B 17/320068* (2013.01); *A61B 17/1615* (2013.01); *A61B 17/1695* (2013.01); *A61B 2017/320072* (2013.01); *A61B 2017/320098* (2017.08); *A61B 2217/005* (2013.01); *A61B 2217/007* (2013.01)

(58) Field of Classification Search
CPC .... A61B 17/320068; A61B 17/320072; A61B 17/320076; A61B 17/320084; A61B 17/1695
See application file for complete search history.

(56) References Cited

U.S. PATENT DOCUMENTS

| 5,275,610 | A  | * | 1/1994  | Eberbach | A61M 29/02 604/105 |
| 6,443,969 | B1 |   | 9/2002  | Novak et al. | |
| 2004/0167625 | A1 | * | 8/2004  | Beyar | A61B 17/1637 623/11.11 |
| 2006/0276816 | A1 | * | 12/2006 | Eckman | A61B 17/320708 606/160 |
| 2007/0067034 | A1 | * | 3/2007  | Chirico | A61B 17/70 623/17.11 |
| 2008/0009877 | A1 | * | 1/2008  | Sankaran | A61B 17/1617 606/84 |
| 2008/0086157 | A1 | * | 4/2008  | Stad | A61B 17/320725 606/167 |
| 2009/0299371 | A1 |   | 12/2009 | Steiner et al. | |
| 2009/0299378 | A1 | * | 12/2009 | Knopp | A61B 17/8811 606/108 |

(Continued)

FOREIGN PATENT DOCUMENTS

| JP | 2009-506845 A | 2/2009 |
| JP | 2009-534155   | 9/2009 |

(Continued)

*Primary Examiner* — Matthew Lawson
(74) *Attorney, Agent, or Firm* — R. Neil Sudol; Henry D. Coleman

(57) ABSTRACT

An ultrasonic surgical drill or drill bit includes a tubular member having a longitudinal axis of symmetry and a plurality of fins extending in longitudinal planes each containing the axis. In a surgical method utilizing the drill bit, one places a distal tip of the drill bit in contact with bone, presses the drill bit against the bone, and during that pressing of the drill bit, conducts ultrasonic vibrations into the drill bit. With the fins in contact with the bone, the drill bit is oscillated or angularly reciprocated about a longitudinal axis, so that the fins fragment bone material located between the fins.

19 Claims, 2 Drawing Sheets

(56) References Cited

U.S. PATENT DOCUMENTS

| | | |
|---|---|---|
| 2009/0318944 A1 | 12/2009 | Kimura et al. |
| 2010/0121197 A1 | 5/2010 | Ota et al. |
| 2012/0179161 A1* | 7/2012 | Rains ................. A61B 17/1617 606/80 |
| 2013/0165935 A1* | 6/2013 | Griffiths ............. A61B 17/1617 606/80 |
| 2015/0265287 A1* | 9/2015 | Berberich .......... A61B 17/1615 606/80 |

FOREIGN PATENT DOCUMENTS

| | | |
|---|---|---|
| JP | 2009-261667 A | 11/2009 |
| JP | 2010-504138 A | 2/2010 |
| WO | WO 2007/028140 A2 | 3/2007 |
| WO | WO 2007/133240 A2 | 11/2007 |
| WO | WO 2008/038307 A1 | 4/2008 |
| WO | WO 2009-141634 A1 | 11/2009 |
| WO | WO 2011-132876 A2 | 10/2011 |

\* cited by examiner

ULTRASONIC SURGICAL DRILL AND ASSOCIATED SURGICAL METHOD

FIELD OF THE INVENTION

This invention relates to an ultrasonic cutting blade. More particularly, this invention relates to an ultrasonic rotary blade or drill. The blade or drill is particularly useful in surgical applications to incise bone tissue.

BACKGROUND OF THE INVENTION

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade which has teeth arranged around its circumference similar to a table saw blade. All of these traditional bone saws are used today in medical procedures around the world.

In many surgical operations it is necessary to obtain direct access to the cranial cavity and the brain. To perform such operations it is often necessary to drill holes through the skull bone. Since the bone is very hard, it is necessary to apply significant pressure to drill through it. Since the dura beneath the skull bone and the brain itself are very delicate, it is difficult to prevent the dura from being cut or damaged when using conventional rotary drills, whether manually or automatically powered and controlled.

In the past, surgeons have used hand braces and bits of a design very similar to those used for non-medical purposes, for example carpentry. Such tools are not completely satisfactory because it has been found that such tools can cut through the skull and damage the meninges or brain and tend not to leave the skull or the underlying membranes in a condition that enables them to heal to approximately their original condition.

It has been found that ultrasonic blades, if properly designed and properly used, can cut bone without damaging the soft tissue adjacent the bone. U.S. Patent Application Publication No. 20050273127 by Novak et al. discloses a surgical blade and a related method of use of that surgical blade in an ultrasonically assisted procedure for cutting bone, wherein adjacent soft tissue is not damaged. The observation was made that the sharper the blade, i.e., the smaller the minor dimension of a vertical trapezoid formed by the included angle of a blade of width N, the more likely that cutting of hard tissues resulted in collateral damage, particularly incisions, in surrounding soft tissue. It was discovered that blades with an edge thickness between approximately 0.001" and approximately 0.010" inch offered the best compromise between effective, safe cutting of hard tissue such as bone while being sparing of surrounding soft tissue.

The teachings of U.S. Patent Application Publication No. 20050273127 pertain to linear cutting blades moved by a reciprocating sawing-type motion, and not to rotary tools. Drilling into bone evidently requires its own protective technique and associated tool for minimizing or avoiding damage to brain tissues.

OBJECTS OF THE INVENTION

It is an object of the present invention to provide an improved ultrasonic drill.

More particularly, it is an object of the present invention to provide an improved ultrasonic drill bit or head.

An even more particular object of the present invention is to provide such an ultrasonic drill bit or head for drilling into bone such as a skull.

A related object of the present invention is to provide an associated method for drilling into bone tissue, including skull tissue.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

An ultrasonic surgical instrument in accordance with the present invention comprises a tubular member having a longitudinal axis of symmetry and a plurality of fins connected to the tubular member and extending in longitudinal planes each containing the axis. Each of the fins has a distal end portion and a proximal end portion, where the distal end portion is spaced from a distal tip of the tubular member. The distal end portion of each fin has a width, extending in the respective longitudinal plane and measured in a radial direction relative to the axis, that increases with increasing distance from the distal tip. Thus, the distal end portion of each fin has a maximum width at a proximal end. The proximal end portion of each fin has a width, extending in the longitudinal plane of the respective fin and measured in a radial direction relative to the instrument axis, that decreases with increasing distance from the distal tip of the instrument. Accordingly, the proximal end portion of each fin has a maximum width at a distal end. The maximum width of the distal end portion and the maximum width of the proximal end portion are equal.

Preferably, the fins are between three and twelve in number and are angularly equispaced about the tubular member or shaft.

Pursuant to a particular embodiment of the present invention, the distal end portion of each of the fins is triangular and has a linear outer edge extending from an outer surface of the tubular member at a distal side to a point at the first maximum width on a proximal side. Concomitantly, in this particular embodiment of the invention, the proximal end portion of each fin has a curvilinear outer edge extending from the maximum width at the distal end of the proximal end portion to an outer surface of the tubular member at a proximal end of the proximal end portion. Preferably, the curvilinear edge is concave.

In a modified embodiment of the invention, the distal end portion of one or more fins might have an outer edge that is arcuate and concave. In another modification of the invention, the proximal end portion of one or more fins might have an outer edge that is straight or linear. Alternatively, the distal end portion of one or more fins might have an outer edge that is at least partially arcuate and convex. Alternatively, the proximal end portion of one or more fins might have an outer edge that is at least partially arcuate and convex.

It is contemplated that an ultrasonic surgical drill in accordance with the present invention, is provided with a sheath extending over the proximal end portions of the fins at least to the maximum width, that is, the proximal boundary of the distal end portions of the fins.

A surgical method in accordance with the present invention utilizes a drill bit having a plurality of at least partially longitudinally extending fins angularly spaced from each other about an instrument shaft. The method comprising providing the drill bit, placing a distal tip of the drill bit in contact with bone, pressing the drill bit against the bone, and during that pressing of the drill bit, conducting ultrasonic vibrations into the drill bit. In addition, with the fins in contact with the bone, the drill bit is oscillated or angularly reciprocated about a longitudinal axis, so that the fins fragment bone material located between the fins.

It is contemplated that the ultrasonic vibrations include at least longitudinal compression waves. Pursuant to a feature of the invention, the ultrasonic vibrations that energize the drill bit may further include torsional (twisting) waves. In the latter case, the longitudinal compression waves and torsional waves may be applied simultaneously.

Pursuant to another feature of the present invention, the oscillating or reciprocating of the drill bit and the pressing of the drill bit against the bone are performed in a staggered sequence. Thus, the oscillating or reciprocating of the drill bit and the pressing of the drill bit against the bone may be at different, nonoverlapping or alternating times or, alternatively, may be partially overlapping. In the latter case, the pressing of the drill bit occurs during a first interval and the oscillating or reciprocating of the drill bit occurs in a second interval, the second interval partially overlapping the first interval.

Where the method includes several or more cycles of ultrasonic vibration and oscillating or reciprocating, the actions may overlap in each cycle. Thus, where the pressing of the drill bit against the bone occurs during multiple first intervals and the oscillating or reciprocating of the drill bit occurs in multiple second intervals, each of the second intervals may partially overlap at least one of the first intervals.

The pressing of the drill bit against the bone may include manually pushing the drill bit against the bone and the oscillating or reciprocating of the drill bit may include manually turning the drill bit. Alternatively, one or the other action or both may be done with the aid of a motor, hydraulic or pneumatic cylinder, solenoid or other mechanism.

It is to be understood that the oscillating or reciprocating of the drill bit has a repetition frequency substantially less than ultrasonic frequencies. While the ultrasonic frequencies are as high as 20,000 Hz, the oscillating or reciprocating or the drill bit may occur no more than a 5-10 times per second or less, if the action is manually powered. Thus, the oscillating or reciprocating of the drill bit may consist of a macro-metric motion of the drill bit.

DETAILED DESCRIPTION

Figure 1:
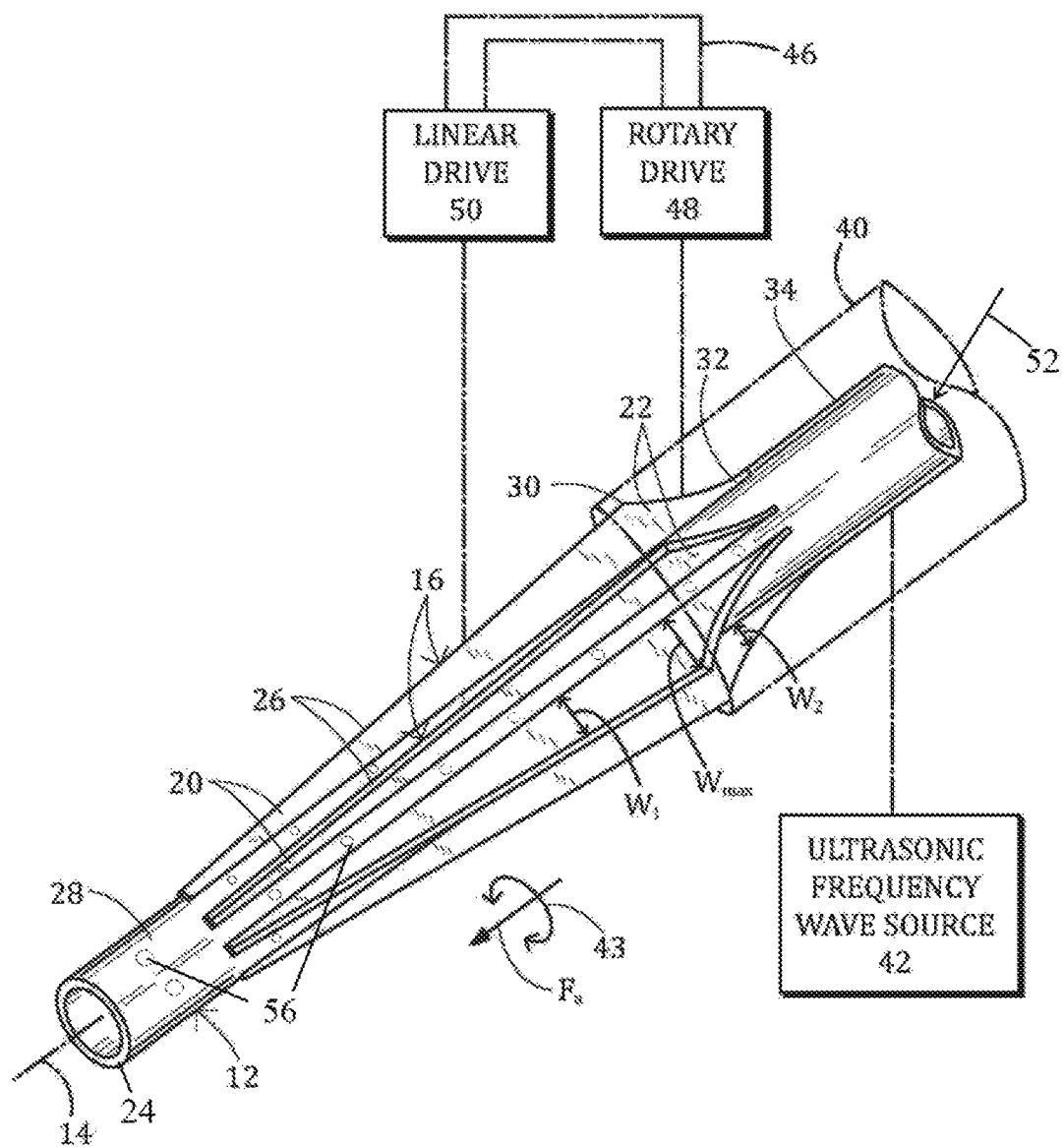
FIG. 1 is a schematic perspective view of a distal end portion of an ultrasonic bone drill, or drill bit, in accordance with the present invention.
Figure 2:
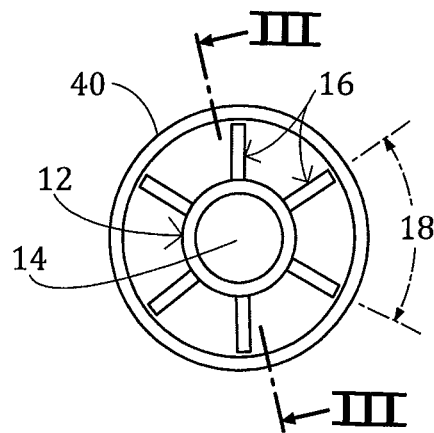
FIG. 2 is a schematic front elevational view of the drill bit of FIG. 1.
Figure 3:
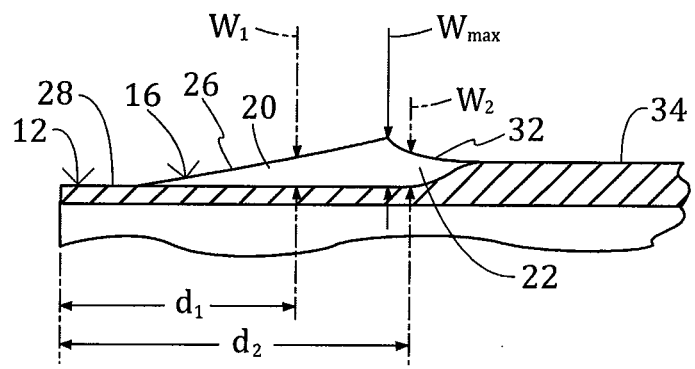
FIG. 3 is a schematic partial longitudinal cross-sectional view, taken along line in FIG. 2.

As depicted in FIGS. 1-3, an ultrasonic surgical drill or drill bit comprises a tubular member 12 having a longitudinal axis of symmetry 14 and a plurality of fins 16 connected to and integral with the tubular member. Fins 16 are solid plate members that extend in longitudinal planes 18 each containing the axis. Each fin 16 has a distal end portion 20 and a proximal end portion 22, where the distal end portion 20 is spaced from a distal tip 24 of the tubular member. The distal end portion 20 of each fin 16 has a width $w_1$, extending in the respective longitudinal plane 18 and measured in a radial direction perpendicularly to axis 14, that increases with increasing distance $d_1$ from distal tip 24. In other words, the greater the longitudinal or axial distance $d_1$ from tip 24, the greater the width $w_1$ of distal end portion 20 of each fin 16. In mathematical parlance, the fin width $w_1$ increases monotonically as a function of the distance $d_1$. Accordingly, the distal end portion 20 of each fin 16 has a maximum width $W_{max}$ at a proximal end.

The proximal end portion 22 of each fin 16 has a width $w_2$, extending in the longitudinal plane 18 of the respective fin 16 and measured in a radial direction relative to the instrument axis 14, that decreases with increasing distance $d_2$ from the distal tip of the instrument. Thus, the greater the longitudinal or axial distance $d_2$ from tip 24, the smaller the width $w_2$ of proximal end portion 22 of each fin 16. In mathematical parlance, the fin width $w_2$ decreases monotonically as a function of the distance $d_2$. Accordingly, the proximal end portion 22 of each fin 16 has maximum width $W_{max}$ at a distal end. Owing to the contiguity of distal fin portion 20 and proximal fin portion 22, maximum width $W_{max}$ is the same for the two end portions 20 and 22 of each fin.

Preferably, fins 16 are between three and twelve in number and are angularly equispaced about the tubular member or shaft. However, it is to be noted that the larger the number of fins 16, the larger the contact area and the larger the force needed to drive the fins 16 into bone. A bone drilling operation is envisioned to be a mix between an axial displacement needed to drive the drill into the bone over a relatively short distance, approx 0.5 mm and a small sector motion around the drill's central axis 14, intended to help with breaking the bone structure located between the fins 16. In order to reduce the possibility of a tool jam, the fin's root diameter should be the same all the way to the transition into the proximal portion 22 of the fins 16 or even at a negative angle, in the region of distal fin portions 20.

Distal end portion 20 of each fin 16 is triangular and has a linear outer edge 26 extending from an outer surface 28 of tubular member 12 at a distal side to a point 30 at maximum width $W_{max}$ on a proximal side. Concomitantly, proximal end portion 22 of each fin 16 has a curvilinear outer edge 32 extending from the maximum width $W_{max}$ at the distal end of the proximal end portion to an outer surface 34 of tubular member 12 at a proximal end of the proximal end portion 22. Curvilinear edge 32 may be concave as shown or convex. As indicated below with reference to FIG. 5, edge 32 may be replaced by a linear edge 36. Each fin 16 is a continuous solid member throughout, from 26 linear outer edge radially inwardly to the outer surface 28 of tubular member 12 and likewise from curvilinear outer edge 32 radially inwardly to the tubular member.

FIG. 3 depicts tubular member 12 has having two outer surfaces 28 and 34 of smaller and larger diameter, respectively. However, tubular member 12 may be alternatively configured so that outer surfaces 28 and 34 are of equal diameter.

Figure 4:
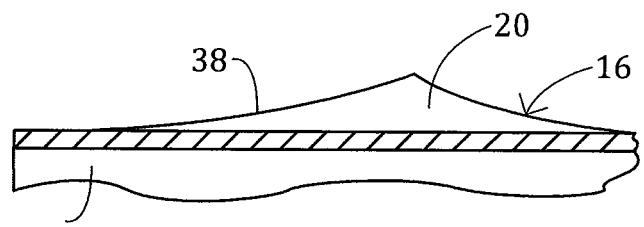
FIG. 4 is a partial cross-sectional view similar to FIG. 3, showing a modified ultrasonic bone drill, or drill bit, in accordance with the present invention.

As depicted in FIG. 4, distal end portion 20 of one or more fins 16 might have an outer edge 38 that is arcuate and concave, for instance, with a degree of curvature that is less that that of outer edge 32 of proximal fin portion 22.

Figure 5:
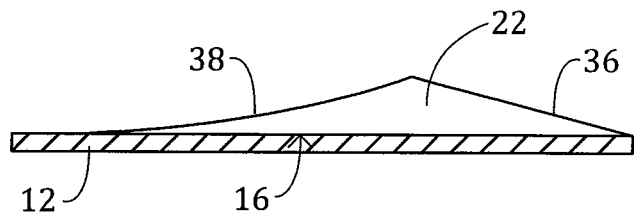
FIG. 5 is a partial cross-sectional view similar to FIG. 3, showing another modified ultrasonic bone drill, or drill bit, in accordance with the present invention.

As shown in FIG. 5, the embodiment of FIG. 4 may be modified so that proximal end portion 22 of one or more fins 16 has straight or linear outer edge 36.

The ultrasonic surgical drill or drill bit is provided with a sheath 40 extending over proximal end portions 22 of fins 16 at least to the maximum width $W_{max}$, that is, the proximal boundary of the distal end portions 20 of the fins 16. Sheath 40 acts as a conduit for irrigation liquid. Sheath 40 may be configured to include two separate fluid conveyance paths, a pressurized-fluid path for conducting irrigation liquid to the distal end portions 20 of the fins and a suction path for conveying debris away the areas between fins 16. The proximal portions 22 of fins 16 represent an evacuation zone where the suction pressure is at a maximum. Accordingly, sheath 40 may consist of two coaxial tubular members (not separately shown) defining a central suction path and an annular pressurization path coaxial therewith.

In a surgical method utilizing the drill or bit of FIGS. 1-5, distal tip 24 of the drill bit is placed in contact with bone, the drill bit is pressed against the bone with an axial force $F_a$, and during that pressing of the drill bit, ultrasonic vibrations from a piezoelectric, magneto-constrictive or other ultrasonic frequency source 42 are conducted into the drill bit. In addition, with fins 16 in contact with the bone, the drill bit is oscillated or angularly reciprocated about longitudinal axis 14 (arrow 43) so that the fins 16 fragment bone material located between the fins. Typically, the drill is oscillated or turned during the conducting of the ultrasonic vibrations into the drill, and consequently into the bone.

The ultrasonic vibrations, standing waves, are typically longitudinal compression waves. However, the ultrasonic vibrations that energize the drill bit may further include torsional (twisting) waves. In the latter case, the longitudinal compression waves and torsional waves are applied simultaneously. The micro-metric longitudinal and angular vibratory motions are inextricably linked. The geometry of the resonator sets the ratio between the longitudinal and angular displacements. The limits of the combined motion are determined by the resonator material strength.

The oscillating or reciprocating of the drill bit and the pressing of the drill bit against the bone may be manually executed. Alternatively, these actions may be implemented with the aid of a robotic arm 46 having a reciprocating rotary drive 48 and a linear or translational power source 50.

The oscillating or turning of the drill bit and the pressing of the ultrasonically vibrating drill bit against the bone are typically performed in a staggered sequence. the oscillating or turning of the drill and the pressing of the vibrating drill bit against the bone may be at different, nonoverlapping times or, alternatively, may be partially overlapping. In the latter case, the pressing of the vibrating drill bit occurs during a first interval and the oscillating or reciprocating of the drill bit occurs in a second interval, the second interval partially overlapping the first interval.

Where the method includes several or more cycles of ultrasonic vibration and oscillating or reciprocating, the actions may overlap in each cycle. Thus, where the pressing of the drill bit against the bone occurs during multiple first intervals and the oscillating or reciprocating of the drill bit occurs in multiple second intervals, each of the second intervals may partially overlap at least one of the first intervals.

It is to be understood that the oscillating or angular reciprocating of the drill bit has a repetition frequency substantially less than ultrasonic frequencies. While the ultrasonic frequencies (both longitudinal and torsional) are between 20,000 Hz and 55,000 Hz, with a preferred frequency of about 22,500 Hz, the oscillating or angular reciprocating or the drill bit may occur no more than a 5-10 times per second or less, particularly if the action is manually powered. Thus, the oscillating or reciprocating of the drill bit may consist of a macro-metric motion of the drill bit. With rotary drive 48 and a linear or translational power source 50, the oscillating or angular reciprocating or the drill bit may have a higher cycling rate, for example, up to 100 Hz.

The amplitude of the longitudinal ultrasonic vibrations at tip 24 are typically of the order of 200-300 microns. If torsional vibrations are used, the angular amplitudes along the outer edges would be no greater than about 30% of the longitudinal distances, that is up to about 90-100 microns.

Fins 16 have a length of 3-10 mm, with a preferred length of 5 mm, and a thickness of 0.18 to 0.25 mm (0.007 to 0.010 inch). Fins 16 may each have a varying thickness t (FIG. 2) that has a maximum value $t_{max}$ (not indicated in drawing) at the distal end of the respective fin and a minimum value $t_{min}$ at the proximal end of the respective fin. Such a variation in thickness helps to reduce the contact area between the drill bit and the target tissue. Such reduction increases the pressure at the drill-tissue interface for a given driving force.

It is to be noted that the macro-metric axial forward motion (pressing of the drill) can be alternated with an axial motion in the opposite direction (limited retraction or withdrawal of the drill). This alternating macro-metric axial motion tends to improve the access of cooling media at the tool-tissue interface.

An alternate or additional irrigation path entails the introduction of irrigation fluid at 52 through a lumen or central channel 54 of tubular member 12. Tubular member 12 is provided with a plurality of irrigation ports or outlets 56 distributed along the length of the drill bit.

Although the invention has been described in terms of particular embodiments and applications, one of ordinary skill in the art, in light of this teaching, can generate additional embodiments and modifications without departing from the spirit of or exceeding the scope of the claimed invention. For instance, it is contemplated that fins 16 are geometrically identical. However, it is possible that there is some variation in size and shape across the fins 16. In one potential alternative embodiment, there are two sets of fins alternating with one another about the circumference of tubular member 12, with members of one set having one characteristic size and shape and members of the other set having an identical geometry which is different in some respect from the geometry of the first set of fins.

In another variation, distal end portion 20 of one or more fins 16 might have an outer edge that is partially concave, partially convex, and/or partially linear. Alternatively or additionally, proximal end portion 22 of one or more fins 16 might have an outer edge that is similarly a combination of concave, convex and linear.

Accordingly, it is to be understood that the drawings and descriptions herein are proffered by way of example to facilitate comprehension of the invention and should not be construed to limit the scope thereof.

What is claimed is:

1. An ultrasonic surgical instrument assembly for drilling a through hole in hard bone tissue, comprising: an ultrasonic-frequency power source: and
    a drill or drill bit operatively connected to said power source for ultrasonically vibrating in response to an ultrasonic waveform from said power source, said drill or drill bit including:
    a tubular member having an outer surface and a longitudinal axis of symmetry; and
    a plurality of fins connected continuously to said outer surface of said tubular member and extending radially outward from said outer surface in longitudinal planes each containing said axis, said tubular member and said fins being adapted to transmit ultrasonic vibratory energy and to ablate bone tissue by means of the ultrasonic vibratory energy,
    each of said fins having a distal end portion and a proximal end portion,
    said distal end portion being spaced proximally from a distal tip of said tubular member,
    said distal end portion having a width, in the respective longitudinal plane and measured in a radial direction relative to said axis, that increases with increasing distance from said distal tip,
    said distal end portion having a maximum width at a proximal end, said proximal end portion having a width, in the respective longitudinal plane and measured in a radial direction relative to said axis, that decreases with increasing distance from said distal tip,
    said proximal end portion having a maximum width at a distal end,
    the maximum width of said distal end portion and the maximum width of said proximal end portion being equal.

2. The surgical instrument assembly defined in claim 1 wherein the distal end portion of each of said fins is triangular, with a linear outer edge extending from an outer surface of said tubular member at a distal side to a point at said first maximum width on a proximal side.

3. The surgical instrument assembly defined in claim 2 wherein the proximal end portion of each of said fins has a curvilinear outer edge extending from the maximum width at the distal end of said proximal end portion to an outer surface of said tubular member at a proximal end of said proximal end portion.

4. The surgical instrument assembly defined in claim 3 wherein said curvilinear edge is concave.

5. The surgical instrument assembly defined in claim 4 wherein said fins are between three and twelve, inclusive, in number.

6. The surgical instrument assembly defined in claim 5 wherein said fins are angularly equispaced about said axis.

7. The surgical instrument assembly defined in claim 3 wherein each of said fins is a continuous solid member throughout, from said linear outer edge inwardly to said tubular member and from said curvilinear outer edge inwardly to said tubular member.

8. The surgical instrument assembly defined in claim 1, further comprising a sheath extending over said proximal end portion at least to said maximum width, said sheath cooperating with said tubular member to define a path or channel for the conduction of irrigation fluid.

9. The instrument assembly defined in claim 1 wherein each of said fins has a thickness that varies from a maximum thickness value at a distal end of the respective fin and a minimum value at the proximal end of the respective fin.

10. The surgical instrument assembly defined in claim 1 wherein said tubular member has a lumen and is provided with a plurality of mutually spaced apertures serving as irrigation ports directing fluid between said lumen and an outer side of said tubular member.

11. The surgical instrument assembly defined in claim 1 wherein each of said fins is a continuous solid member throughout.

12. The surgical instrument assembly defined in claim 1 wherein each of said fins is a continuous solid member throughout, from an outer edge spaced from said tubular member to an outer surface of said tubular member.

13. The surgical instrument assembly defined in claim 1 wherein each of said fins is a continuous solid plate member.

14. An ultrasonic surgical instrument assembly for drilling a through hole in hard bone tissue, comprising:
    an ultrasonic-frequency power source: and
    a drill or drill bit operatively connected to said power source for ultrasonically vibrating in response to an ultrasonic waveform from said power source, said drill or drill bit including:
    a tubular member having an outer surface and a longitudinal axis of symmetry; and
    a plurality of fins in the form of continuous solid planar plate members connected to said tubular member and extending radially outward from said outer surface in longitudinal planes each containing said axis, said tubular member and said fins being adapted to transmit ultrasonic vibratory energy and to ablate bone tissue by means of the ultrasonic vibratory energy.

15. The surgical instrument assembly defined in claim 14 wherein each of said fins includes a triangular distal end portion, with a linear outer edge extending from an outer surface of said tubular member at a distal side to a point at a maximum fin width on a proximal side.

16. The surgical instrument assembly defined in claim 15 wherein each of said fins includes a proximal end portion having a curvilinear outer edge extending from the point of maximum fin width at the distal end of said proximal end portion to an outer surface of said tubular member at a proximal end of said proximal end portion.

17. The surgical instrument assembly defined in claim 16 wherein said curvilinear edge is concave.

18. The surgical instrument assembly defined in claim 14 wherein said fins are angularly equispaced about said axis.

19. The surgical instrument assembly defined in claim 14, further comprising a sheath extending over at least a proximal end portion of said fins, said sheath cooperating with said tubular member to define a path or channel for the conduction of irrigation fluid.

* * * * *